(12) United States Patent
Ammermann et al.

(10) Patent No.: US 7,732,374 B2
(45) Date of Patent: *Jun. 8, 2010

(54) FUNGICIDAL MIXTURES BASED ON PROTHIOCONAZOLE AND AN INSECTICIDE

(75) Inventors: Eberhard Ammermann, Heppenheim (DE); Reinhard Stierl, Freinsheim (DE); Gisela Lorenz, Neustadt (DE); Siegfried Strathmann, Limburgerhof (DE); Klaus Schelberger, Gönnheim (DE); V. James Spadafora, Sugar Land, TX (US); Thomas Christen, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 294 days.

This patent is subject to a terminal disclaimer.

(21) Appl. No.: 11/778,784

(22) Filed: Jul. 17, 2007

(65) Prior Publication Data

US 2008/0269171 A1  Oct. 30, 2008

Related U.S. Application Data

(62) Division of application No. 10/506,502, filed on Sep. 3, 2004, now Pat. No. 7,375,059.

(30) Foreign Application Priority Data

Mar. 8, 2002 (DE) .................. 102 10 135
Mar. 4, 2003 (WO) ............. PCT/EP03/02191

(51) Int. Cl.
  *A01N 25/26* (2006.01)
  *A01N 57/00* (2006.01)
  *A01N 43/72* (2006.01)
  *A01N 43/653* (2006.01)
  *A01N 43/64* (2006.01)
  *A61K 31/535* (2006.01)

(52) U.S. Cl. ............. 504/100; 504/195; 504/223; 504/273; 514/90; 514/229.2; 514/384

(58) Field of Classification Search ......... 504/128, 504/130, 139, 100, 195, 223, 273; 514/90, 514/229.2, 384
See application file for complete search history.

(56) References Cited

U.S. PATENT DOCUMENTS

| 3,244,586 | A | 4/1966 | Rigterink et al. ............ 167/33 |
| 5,789,430 | A | 8/1998 | Jautelat et al. ........... 514/272.4 |
| 5,852,012 | A | 12/1998 | Maienfisch et al. ....... 514/229.2 |
| 5,859,039 | A | 1/1999 | Jautelat et al. .............. 514/384 |
| 5,877,194 | A | 3/1999 | Colliot et al. ............... 514/383 |
| 6,022,871 | A | 2/2000 | Maienfisch et al. ....... 514/229.2 |
| 6,306,850 | B1 | 10/2001 | Dutzmann et al. ........ 514/229.2 |
| 6,376,487 | B1 | 4/2002 | Maienfisch et al. ....... 514/229.2 |
| 7,375,059 | B2 * | 5/2008 | Ammermann et al. ...... 504/128 |
| 2002/0173529 | A1 | 11/2002 | Dutzmann et al. .......... 514/383 |
| 2004/0186141 | A1 | 9/2004 | Zimmerman ................ 514/341 |

FOREIGN PATENT DOCUMENTS

| CA | 2324464 | 9/1999 |
| DE | 195 48 873 | 7/1997 |
| DE | 199 48 590 | 4/2001 |
| FR | 2712144 | 5/1995 |
| JP | 09/315906 | 12/1997 |
| WO | WO 96/16048 | 5/1996 |
| WO | WO 98/47367 | 10/1998 |
| WO | WO 99/48366 | 9/1999 |
| WO | WO 99/48368 | 9/1999 |

OTHER PUBLICATIONS

Fischer et al., "*Synergistic fungicidal and acaricidal composition, especially useful for plant protection, contains cyclic ketosol and other active agent(s), e.g. fluquiconazole, maneb, captan, sulfur or copper*"; Oct. 8, 1999 (1) esp@cenet English language abstract of document (AC) (2) Derwent English language abstract of document (AC).

Yumi, "*Fungicidal and insecticidal composition*"; Patent Abstracts of Japan, English language abstract of document (AE), Sep. 12, 1997.

Tomlin, "The Pesticide Manual," The British Crop Protection Council 2000, pp. 413-415 regarding "fipronil", Nov. 2, 2000.

* cited by examiner

*Primary Examiner*—Alton N Pryor
(74) *Attorney, Agent, or Firm*—Novak Druce + Quigg LLP

(57) ABSTRACT

A fungicidal mixture comprising prothioconazole or its salts or adducts and at least one insecticide selected from the group consisting of fipronil, chlorpyrifos or thiamethoxam.

11 Claims, No Drawings

FUNGICIDAL MIXTURES BASED ON PROTHIOCONAZOLE AND AN INSECTICIDE

This is a divisional application of application Ser. No. 10/506,502, filed on Sep. 3, 2004 now U.S. Pat. No. 7,375,059, the entire disclosure of which is herewith incorporated by reference, which is a national stage under 35 U.S.C. §371 of international application No. PCT/EP 03/02191, filed on Mar. 4, 2003.

The present invention relates to fungicidal mixtures, comprising
(1) 2-[2-(1-chlorocyclopropyl)-3-(2-chlorophenyl)-2-hydroxypropyl]-2,4-dihydro-[1,2,4]-triazole-3-thione (prothioconazole) of the formula I or its salts or adducts

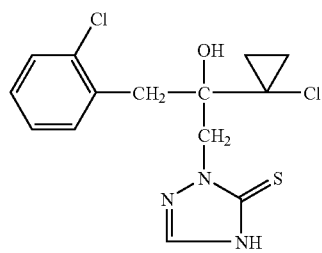

(I)

and at least one insecticide selected from the group consisting of
(2) fipronil of the formula II

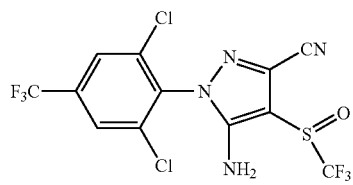

(II)

or
(3) chlorpyrifos of the formula III

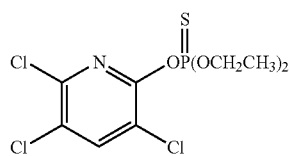

(III)

or
(4) thiamethoxam of the formula IV

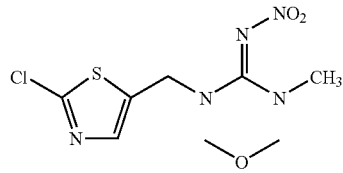

(IV)

in a synergistically effective amount.

Moreover, the invention relates to a method for controlling harmful fungi using mixtures of the compound I with at least one of the compounds II, III or IV and to the use of compounds I, II, III and IV for preparing such mixtures, and to compositions comprising these mixtures.

The compound of the formula I, 2-[2-(1-chlorocyclopropyl)-3-(2-chlorophenyl)-2-hydroxypropyl]-2,4-dihydro-[1,2,4]-triazole-3-thione (prothioconazole) is already known from WO 96/16048.

WO 98/47367 discloses a number of active compound combinations of prothioconazole with a large number of other fungicidal compounds.

Fipronil of the formula II is described in Pest. Man. 12th Ed. (2000), page 413.

Chlorpyrifos of the formula III is also already known and has been described in DE-A-1 445 659.

Finally, thiamethoxam of the formula IV is likewise known and has been described in EP-A 580553.

It is an object of the present invention to provide mixtures which have improved activity against harmful fungi combined with a reduced total amount of active compounds applied (synergistic mixtures), with a view to reducing the application rates and improving the activity spectrum of the known compounds I, II, III and IV.

We have found that this object is achieved by the mixture, defined at the outset, of prothioconazole with at least one insecticide. Moreover, we have found that applying the compound I simultaneously, that is together or separately, with at least one further compound II, III or IV or applying the compound I with at least one of the compounds II, III or IV in succession provides better control of harmful fungi than is possible with the individual compounds alone.

2-[2-(1-Chlorocyclopropyl)-3-(2-chlorophenyl)-2-hydroxypropyl]-2,4-dihydro-[1,2,4]-triazole-3-thione of the formula I is known from WO 96-16 048. The compound can be present in the "thiono" form of the formula

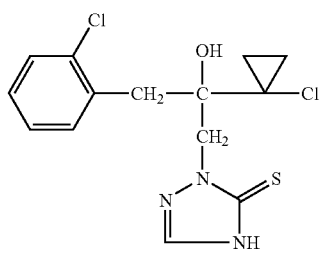

(I)

or in the tautomeric "mercapto" form of the formula

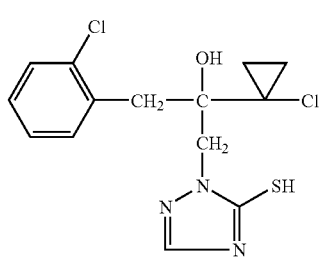

(Ia)

For the sake of simplicity, only the "thiono" form is shown in each case.

Fipronil of the formula II

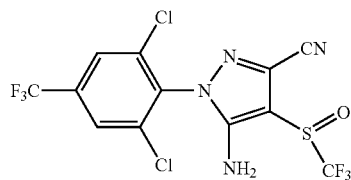

(II)

is described in Pest. Man. 12th Ed. (2000), page 413. Chlorpyrifos of the formula III

(III)

is described in DE-A-1 445 659.

Thiamethoxam of the formula IV

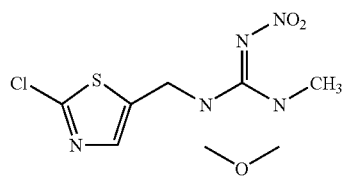

(IV)

is described in EP-A-580 553.

Owing to the basic character of its nitrogen atoms, the compound I is capable of forming salts or adducts with inorganic or organic acids or with metal ions.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid, carbonic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or -disulfonic acids (aromatic radicals, such as phenyl and naphthyl, which carry one or two sulfonic acid groups), alkyl phosphonic acids (phosphonic acids having straight-chain or branched alkyl radicals of 1 to 20 carbon atoms), arylphosphonic acids or -diphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the transition groups of the fourth period. The metals can be present in the various valencies that they can assume.

Preference is given to mixtures of prothioconazole with fipronil.

Furthermore, preference is also given to mixtures of prothioconazole with chlorpyrifos.

Preference is also given to mixtures of prothioconazole with thiamethoxam.

Preference is also given to three-component mixtures of prothioconazole with two of the abovementioned insecticides.

When preparing the mixtures, it is preferred to employ the pure active compounds I, II, III and IV, to which may be added further active compounds against harmful fungi or against other pests, such as insects, arachnids or nematodes, or else herbicidal or growth-regulating active compounds or fertilizers.

The mixtures of the compound I with at least one of the compounds II, III and IV, or the compound I and at least one of the compounds II, III and IV applied simultaneously, together or separately, exhibit outstanding activity against a wide range of phytopathogenic fungi, in particular from the classes Ascomycetes, Basidiomycetes, Phycomycetes and Deuteromycetes. Some of them act systemically and can therefore also be employed as foliar-and soil-acting fungicides.

They are especially important for controlling a large number of fungi in a variety of crop plants, such as cotton, vegetable species (for example cucumbers, beans, tomatoes, potatoes and cucurbits), barley, grass, oats, bananas, coffee, corn, fruit species, rice, rye, soya, grapevine, wheat, ornamentals, sugarcane, and a large number of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and also *Fusarium* and *Verticillium* species.

They can furthermore be employed in the protection of materials (e.g. the protection of wood), for example against Paecilomyces variotil.

The compound I and at least one of the compounds II, III and IV can be applied simultaneously, that is together or separately, or in succession, the sequence, in the case of separate application, generally not having any effect on the result of the control measures.

The compounds I and II are usually employed in a weight ratio of from 20:1 to 1:20, in particular from 10:1 to 1:10, preferably from 5:1 to 1:5.

The compounds I and III are usually employed in a weight ratio of from 20:1 to 1:20, in particular from 10:1 to 1:10, preferably from 5:1 to 1:5.

The compounds I and IV are usually employed in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably from 0.1 to 5 kg/ha, in particular from 0.1 to 3.0 kg/ha.

The application rates of the compounds I are accordingly from 0.01 to 1 kg/ha, preferably from 0.05 to 0.5 kg/ha, in particular from 0.05 to 0.3 kg/ha.

The application rates of the compounds II are accordingly from 0.01 to 1 kg/ha, preferably from 0.02 to 0.5 kg/ha, in particular from 0.05 to 0.3 kg/ha.

The application rates of the compounds III are accordingly from 0.01 to 1 kg/ha, preferably from 0.02 to 0.5 kg/ha, in particular from 0.05 to 0.3 kg/ha.

The application rates of the compounds IV are accordingly from 0.01 to 1 kg/ha, preferably from 0.02 to 0.5 kg/ha, in particular from 0.05 to 0.3 kg/ha.

For seed treatment, the application rates used of the mixture are generally from 0.001 to 250 g/kg of seed, preferably from 0.01 to 100 g/kg, in particular from 0.01 to 50 g/kg.

If phytopathogenic harmful fungi are to be controlled, the separate or joint application of the compound I and at least one of the compounds II, III and IV or of the mixtures of the compound I with at least one of the compounds II, III or IV is effected by spraying or dusting the seeds, the plants or the soils before or after sowing of the plants, or before or after plant emergence.

The fungicidal synergistic mixtures according to the invention or the compound I and at least one of the compounds II, III and IV can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, for example by adding solvents and/or carriers. The formulations are usually admixed with inert additives, such as emulsifiers or dispersants.

Suitable surfactants are the alkali metal salts, alkaline earth metal salts and ammonium salts of aromatic sulfonic acids, for example ligno-, phenol-, naphthalene-and dibutylnaphthalenesulfonic acid, and of fatty acids, alkyl-and alkylarylsulfonates, alkyl, lauryl ether and fatty alcohol sulfates, and also salts of sulfated hexa-, hepta-and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl-or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders, materials for broadcasting and dusts can be prepared by mixing or jointly grinding the compound I and at least one of the compounds II, III or IV or the mixture of the compound I with at least one of the compounds II, III or IV with a solid carrier.

Granules (for example coated granules, impregnated granules or homogeneous granules) are usually prepared by binding the active compound or active compounds to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic minerals, and also fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of the compound I and at least one of the compounds II, III or IV or of the mixture of the compound I with at least one of the compounds II, III or IV. The active compounds are employed in a purity of from 90% to 100%, preferably from 95% to 100% (according to NMR spectrum or HPLC).

The compounds I, II, III and IV, the mixtures, or the corresponding formulations, are applied by treating the harmful fungi, their habitat, or the plants, seeds, soils, areas, materials or spaces to be kept free from them with a fungicidally effective amount of the mixture, or of the compound I and at least one of the compounds II, III or IV in the case of separate application.

Application can be effected before or after infection by the harmful fungi.

USE EXAMPLE

The synergistic activity of the mixtures according to the invention was demonstrated by the following experiments:

The active compounds, separately or together, were formulated as a 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (W) was calculated as follows using Abbot's formula:

$$W = \left(1 - \frac{\alpha}{\beta}\right) \cdot 100$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

Colby formula: $E = x + y - x \cdot y/100$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b Use Example 1

Protective Activity Against Mildew of Cucumbers Caused by *Sphaerotheca fuliginea*

Leaves of potted cucumber seedlings of the cultivar "Chinese Snake", in the cotyledon stage, were sprayed to runoff point with an aqueous suspension having the concentration stated below of active compounds. The suspension or emulsion was prepared from a stock solution using 10% of active compound in a mixture of 70% cyclohexanone, 20% of wetting agent and 10% of emulsifier. 20 hours after the spray coating had dried on, the plants were inoculated with an aqueous spore suspension of mildew of cucumbers (*Sphaerotheca fuliginea*). The plants were then cultivated in a greenhouse at 20-24° C. and 60-80% relative atmospheric humidity for 7 days. The extent of mildew development was then determined visually in % infection of the cotyledon area.

The visually determined values for the percentage of infected leaf areas were converted into efficacies in % of the untreated control. An efficacy of 0 means the same degree of infection as the untreated control, an efficacy of 100 means 0% infection. The expected efficacies for active compound combinations were determined using the Colby formula given above and compared to the observed efficacies.

TABLE 1

| Active compound | Concentration of active compound in the spray liquor in ppm | Efficacy in % of the untreated control |
|---|---|---|
| Control (untreated) | (84% infection) | 0 |
| Compound I = prothioconazole | 0.25 | 5 |
|  | 0.06 | 0 |
|  | 0.015 | 0 |
| Compound II = fipronil | 1 | 0 |
|  | 0.25 | 0 |
|  | 0.06 | 0 |
|  | 0.015 | 0 |
| Compound III = chlorpyrifos | 0.25 | 0 |
|  | 0.06 | 0 |
|  | 0.015 | 0 |
| Compound IV = thiamethoxam | 4 | 0 |
|  | 1 | 0 |
|  | 0.25 | 0 |
|  | 0.06 | 0 |
|  | 0.015 | 0 |

TABLE 2

| Combinations according to the invention | Observed efficacy | Calculated efficacy*) |
|---|---|---|
| Compound I = prothioconazole + Compound II = fipronil 0.015 + 0.25 ppm mixture 1:16 | 17 | 0 |
| Compound I = prothioconazole + Compound II = fipronil 0.25 + 1 ppm mixture 1:4 | 64 | 5 |
| Compound I = prothioconazole + Compound II = fipronil 0.25 + 0.06 ppm mixture 4:1 | 29 | 5 |
| Compound I = prothioconazole + Compound II = fipronil 0.25 + 0.015 ppm mixture 16:1 | 64 | 5 |

TABLE 2-continued

| Combinations according to the invention | Observed efficacy | Calculated efficacy*) |
|---|---|---|
| Compound I = prothioconazole + Compound III = chlorpyrifos 0.015 + 0.25 ppm mixture 1:16 | 17 | 0 |
| Compound I = prothioconazole + Compound III = chlorpyrifos 0.06 + 0.25 ppm mixture 1:4 | 29 | 0 |
| Compound I = prothioconazole + Compound III = chlorpyrifos 0.25 + 0.06 ppm mixture 4:1 | 29 | 5 |
| Compound I = prothioconazole + Compound III = chlorpyrifos 0.25 + 0.015 ppm mixture 16:1 | 17 | 5 |
| Compound I = prothioconazole + Compound IV = thiamethoxam 0.25 + 4 ppm mixture 1:16 | 29 | 5 |
| Compound I = prothioconazole + Compound IV = thiamethoxam 0.25 + 1 ppm mixture 1:4 | 76 | 5 |
| Compound I = prothioconazole + Compound IV = thiamethoxam 0.06 + 0.25 ppm mixture 1:4 | 82 | 0 |
| Compound I = prothioconazole + Compound IV = thiamethoxam 0.25 + 0.06 ppm mixture 4:1 | 29 | 5 |
| Compound I = prothioconazole + Compound IV = thiamethoxam 0.25 + 0.015 ppm mixture 16:1 | 17 | 5 |

*)efficacy calculated using Colby's formula

The test results show that, for all mixing ratios, the observed efficacy is higher than the efficacy calculated beforehand using Colby's formula (from Synerg 173. XLS).

We claim:

1. A method for controlling harmful fungi, which comprises treating the harmful fungi, their habitat or plants, seeds, soils, areas, materials or spaces to be kept free from said fungi with a fungicidal mixture comprising synergistically effective amounts of (1) 2-[2-(1-chlorocyclopropyl)-3-(2-chlorophenyl)-2-hydroxypropyl]-2,4-dihydro-[1,2,4]-triazole-3-thione (prothioconazole) of the formula I or its salts or adducts

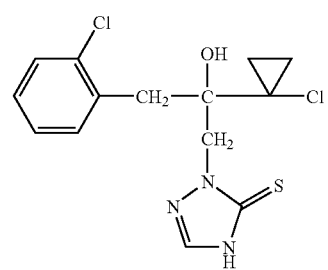

and at least one insecticide selected from the group consisting of (2) fipronil of the formula II

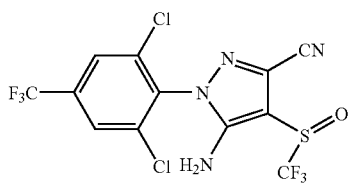

or
(3) chlorpyrifos of the formula III

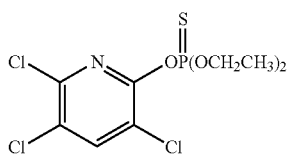

or
(4) thiamethoxam of the formula IV

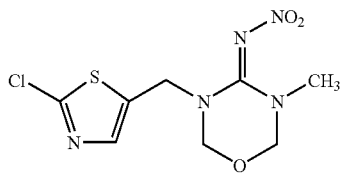

wherein the compound of the formula I and the at least one compound of the formula II, III or IV are applied simultaneously, that is together or separately, or in succession.

2. A method as claimed in claim 1, wherein the fungicidal mixture or the compound of the formula I and the at least one compound of the formula II, III or IV are applied in an amount of from 0.01 to 8 kg/ha.

3. A method as claimed in claim 1, wherein the at least one insecticide is fipronil of the formula II.

4. A method as claimed in claim 1, wherein the at least one insecticide is chlorpyrifos of the formula III.

5. A method as claimed in claim 1, wherein the at least one insecticide is thiamethoxam of the formula IV.

6. A method as claimed in claim 1, wherein prothioconazole of the formula I and the at least one insecticide are applied at a weight ratio of prothioconazole to fipronil of the formula II is from 20:1 to 1:20, chlorpyrifos of the formula III is from 20:1 to 1:20 and thiamethoxam of the formula IV is from 20:1 to 1:20.

7. A method as claimed in claim 1, wherein prothioconazole of the formula I is applied at an application rate of from 0.01 to 1 kg/ha.

8. A method as claimed in claim 1, wherein fipronil of the formula II is applied at an application rate of from 0.01 to 1 kg/ha.

9. A method as claimed in claim 1, wherein chlorpyrifos of the formula III is applied at an application rate of from 0.01 to 1 kg/ha.

10. A method as claimed in claim 1, wherein thiamethoxam of the formula IV is applied at an application rate of from 0.01 to 1 kg/ha.

11. A method as claimed in claim 1, wherein the fungicidal mixture or the compound of the formula I and the at least one compound of the formula II, III or IV are applied as seed treatment in an amount of from 0.001 to 250 g/kg of seed.

* * * * *